United States Patent
Pruche et al.

(12) 
(10) Patent No.: US 6,468,972 B1
(45) Date of Patent: *Oct. 22, 2002

(54) METHOD TO PROMOTE, STIMULATE AND/OR DELAY HAIR LOSS BY A BRADY KININ ANTAGONIST

(75) Inventors: Francis Pruche; Albert Duranton; Nathalie Boyera, all of Paris; Brigitte Gautier, Les Ulis, all of (FR)

(73) Assignee: Societe L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 25 days.

(21) Appl. No.: 08/981,279

(22) PCT Filed: Oct. 1, 1996

(86) PCT No.: PCT/FR96/01528

§ 371 (c)(1),
(2), (4) Date: Jan. 20, 1998

(87) PCT Pub. No.: WO97/13493

PCT Pub. Date: Apr. 17, 1997

(30) Foreign Application Priority Data

Oct. 6, 1995 (FR) ............................................. 95 11809

(51) Int. Cl.⁷ .......................... A61K 37/02; A61K 7/48
(52) U.S. Cl. .............................. 514/15; 514/2; 514/880; 530/328; 424/70.1; 424/401
(58) Field of Search .............................. 514/2, 15, 880; 530/328; 424/70.1, 401

(56) References Cited

U.S. PATENT DOCUMENTS 5,811,395 A * 9/1998 Schwabe et al. ............... 514/12
5,849,312 A * 12/1998 Breton et al. ............... 424/401

FOREIGN PATENT DOCUMENTS

| EP | 0 334 244 | 3/1989 |
|---|---|---|
| EP | 0 370 453 | 11/1989 |
| EP | 0 413 277 | 8/1990 |
| EP | 0 455 133 | 4/1991 |
| EP | 0 472 220 | 8/1991 |
| EP | 0 564 972 | 3/1993 |
| EP | 0 578 521 | 6/1993 |
| EP | 0 623 350 | 4/1994 |
| WO | 86 07263 | 12/1986 |
| WO | 89 01780 | 3/1989 |
| WO | 89 09231 | 10/1989 |
| WO | 90 03980 | 4/1990 |
| WO | 89 09230 | 10/1990 |
| WO | 91 02746 | 3/1991 |
| WO | 91 09055 | 9/1991 |
| WO | 92 17201 | 10/1992 |
| WO | 93 11789 | 6/1993 |
| WO | 94 06453 | 3/1994 |
| WO | 94 11021 | 5/1994 |
| WO | 94 18835 | 9/1994 |
| WO | 95 07294 | 3/1995 |

OTHER PUBLICATIONS

WPIDS AN 91–325577 to BE 1003002, Oct. 1991.*

* cited by examiner

*Primary Examiner*—Bennett Celsa
(74) *Attorney, Agent, or Firm*—Burns, Doane, Swecker & Mathis, L.L.P.

(57) ABSTRACT

The present invention is directed to a method to promote, stimulate and/or delay hair loss by administering an effective amount of at least one bradykinin antagonists to promote, stimulate and/or delay hair loss to an individual in need thereof.

8 Claims, No Drawings

METHOD TO PROMOTE, STIMULATE AND/OR DELAY HAIR LOSS BY A BRADY KININ ANTAGONIST

CROSS-REFERENCE TO RELATES APPLICATIONS

This application claims benefit of priority under 371 to PCT/FR96/01528, filed on Oct. 1, 1996, which in turn claims benefit of priority to French Patent Application No. 95/11809, filed on Oct. 6, 1995.

FIELD OF THE INVENTION

The present invention relates to the use, as active principle, in a physiologically acceptable medium, in a cosmetic composition or for the preparation of a medicinal product, of an effective amount of at least one bradykinin antagonist which is intended to induce and/or stimulate hair growth and/or delay hair loss.

BACKGROUND OF THE INVENTION

In human beings, hair growth and its renewal are mainly determined by the activity of the hair follicles. Their activity is cyclical and comprises essentially three phases, namely the anagenic phase, the catagenic phase and the telogenic phase.

The active anagenic phase or growth phase, which lasts several years and during which the hair grows longer, is followed by a very short and transitory catagenic phase, which lasts a few weeks, and then by a resting phase, known as the telegenic phase, which lasts a few months.

At the end of the resting period, the hair falls out and another cycle recommences. The head of hair is thus constantly renewed and, of the approximately 150,000 hairs which a head of hair contains, at each instant, approximately 10% of them are at rest and will therefore be replaced in a few months.

In a significant number of cases, early hair loss takes place in subjects who are genetically predisposed to it and it affects men in particular. It is more particularly androgenetic in character or is referred to as androgenic alopecia or alternatively androgeno-genetic alopecia.

This alopecia is essentially due to a disturbance in hair renewal which results, at first, in an acceleration in the frequency of the cycles at the expense of the quality of the hair and then of its amount. A progressive thinning of the head of hair takes place by regression of the so-called "terminal" hairs to the downy stage. Regions are preferentially affected, in particular the temple or frontal bulbs in men and, in women, a diffuse alopecia of the vertex is observed.

The term alopecia covers a whole family of complaints of the hair follicle, whose final consequence is the partial or general permanent loss of the hair. Mention may be made, for example, of androgenic alopecia.

A search has been under way for many years in the cosmetic or pharmaceutical industry for substances which make it possible to suppress or reduce the effect of alopecia and in particular to decrease hair loss or to induce or to stimulate its growth.

In this perspective, a large number of very diverse active compounds have, admittedly, already been proposed, such as, for example 2,4-diamino-6-piperidinopyrimidine 3-oxide or "Minoxidil" described in U.S. Pat. No. 4,596, 812, or alternatively the many derivatives thereof such as those described, for example, in patent applications EP 0,353,123, EP 0,356,271, EP 0,408,442, EP 0,522,964, EP 0,420,707, EP 0,459,890 and EP 0,519,819.

Mention may also be made of 6-amino-1,2-dihydro-1-hydroxy-2-imino-4-piperidinopyrimidine and the derivatives thereof, which are described more particularly in patent U.S. Pat. No. 4,139,619.

BRIEF DESCRIPTION OF THE INVENTION

It generally remains that it would be advantageous and useful to have available active compounds other than those already known, that are potentially more active and/or less toxic.

Bradykinin is a peptide of plasma origin released from a kininogen precursor by a plasma protease known as kallikrein (EC 3.4.21.24). This nanopeptide is one of the key mediators of inflammation and has mitogenic properties. The receptors for this kinin are divided into two main subtypes, B1 and B2. Bradykinin acts in particular on the B2 receptor and causes the stimulation of many second messenger production systems including the hydrolysis of inositol phosphates, the metabolism of arachidonic acid, the phosphorylation of tyrosine residues and the depolarization or hyperpolarization of the cell membrane.

The activation of certain receptors causes the activation of phospholipase C and thus the production of inositol 1,4,5-triphosphate (IP3) and of diacylglycerol (DAG). IP3 is known to cause the release of calcium from intercellular storage sites in cells, including keratinocytes. Calcium is described as an activator and regulator of many enzymes (proteases, phospholipases) and plays an important part in regulating the differentiation and proliferation of keratinocytes.

Bradykinin is involved in a large number of physiopathological disorders including: hypotension, contraction of the smooth muscles the digestive and respiratory tracts and in the uterus, pain, the proliferation of connective tissue and the release of different inflammation mediators: cytokines, leukotrienes and prostaglandins.

To date, to the Applicant's knowledge, it has neither been envisioned or even suggested that bradykinin receptors exist in the hair follicle, nor that bradykinin plays a part in the phenomena resulting in hair loss and/or hair growth.

Surprisingly and unexpectedly, the Applicant has just discovered that Minoxidil, which is known for its effects on regrowth of the hair and on the storage and/or release of calcium by cells (Matsumoto et al., Nippon Hifuka Gakkai Zasshi (1993), 103(2), 103–15), blocks the increase in the calcium concentration of the intracellular medium induced by bradykinin. The Applicant has also shown that this is likewise the case for Minoxidil sulphate for which there is general agreement in the prior art that this is probably the active derivative of Minoxidil in regrowth of the hair in vivo.

Thus, Minoxidil or derivatives thereof can act as a bradykinin antagonist.

The term bradykinin antagonist is understood to refer to any compound which is capable of partially, or even totally, inhibiting the biological effect of bradykinin, except for the compounds known to have an effect on the storage and/or release of calcium in the cell, such as Minoxidil and derivatives thereof.

Particularly, for a substance to be recognized as a bradykinin antagonist, it must induce a coherent pharmacological response which may or may not include its binding to the bradykinin receptor.

Thus, any compound which can interfere with the effects of bradykinin by binding to the bradykinin receptor (B1 or B2) and/or any compound which, independently of binding to the receptor(s), will induce by whatever mechanism an effect contrary to that known for bradykinin (for example interfering with bradykinin synthesis) falls within this definition.

The use of a bradykinin antagonist can thus be one of the effective routes for controlling hair loss and/or for promoting regrowth of the hair.

This discovery forms the basis of the present invention.

Thus, the invention relates to the use, in a cosmetic composition or for the preparation of a medicinal product, of an effective amount of at least one bradykinin antagonist, this antagonist or the medicinal product being intended to induce and/or stimulate hair growth and/or slow down hair loss.

According to the invention, it is possible to use a single bradykinin antagonist or several together. For example, it is possible to use a release antagonist and/or a synthesis antagonist in combination with a B1 and/or B2 receptor antagonist, for example.

As has been pointed out above, according to the invention, the term bradykinin antagonist is understood to refer to any compound which is capable of partially, or even totally, inhibiting the biological effect of bradykinin, except for the compounds known to have an effect on the storage and/or release of calcium in the cell, such as Minoxidil and derivatives thereof.

Among the bradykinin antagonists, it is preferred to use, for example, compounds which inhibit the synthesis and/or accelerate the catabolism of bradykinin, brady-kinin neutralizers, bradykinin receptor blockers such as those which interfere with the effects of bradykinin by binding to its receptor (B1 or B2), compounds which inhibit the synthesis of bradykinin receptors or compounds involved in modulating the signal transduced by bradykinin. These compounds can be of natural or synthetic origin.

Among the bradykinin antagonists, mention may be made more particularly of optionally modified, natural or synthetic peptides such as D-Arg, [Hyp3, D-Phe7]bradykinin (NPC567), [Thi 5,8, D-Phe7]bradykinin, D-Arg, [Hyp3, Thi5,8, D-Phe7]bradykinin, N-α-adamantaneacetyl-D-Arg, [Hyp3, Thi5,8, D-Phe7]-bradykinin, des-Arg9, [Leu8] bradykinin (which are all sold by the company Sigma) or the compounds mentioned in patents WO 95/08566, WO 95/07294, EP 0,623,350, EP 0,622,361, WO 94/11021, EP 0,596,406, WO 94/06453, WO 94/09001, EP 0,578,521, EP 0,564,972, EP 0,552,106, WO 93/11789, U.S. Pat. No. 5,216,165, U.S. Pat. No. 5,212,182, WO 92/17201, EP 0,496,369, EP 0,472,220, EP 0,455,133, WO 91/09055, WO 91/02746, EP 0,413,277, EP 0,370,453, EP 0,359,310, WO 90/03980, WO 89/09231, WO 89/09230, WO 89/01780, EP 0,334,244, EP 0,596,406, WO 86107263 or P-guanidobenzoyl, [Hyp3, Thi5, D-Tic7, Oic8]bradykinin (S 16118) (Feletou M & al., Pharmacol. Exp. Ther., June 1995, 273, 1078–84), D-Arg, [Hyp3, Thi5, D-Tic7, Oic8]-bradykinin (HOE 140) (Feletou M & al., Eur. J. Phannacol, 1995, 274, 57–64), D-Arg. [Hyp3, D-Hype (trans-propyl)7, Oic8]bradykinin (NPC 17731) (Herzig M. C. S. and Leeb-Lundberg L. M. F., J. Biol. Chem. 1995, 270, 20591–20598) or those mentioned in Bradykinin Antagonists: development and applications (Stewart J. M., Biopolymers, 1995, 37, 143–155), or alternatively natural or synthetic chemical molecules such as, for example, those described in Salvino et al., J. Med. Chem., 1993, 36,2583–2584.

According to the invention, it is also possible to use antisense nucleic acid or ribozymes whose aim is to selectively inhibit bradykinin synthesis. These antisense nucleic acids are known to those skilled in the art. They can act in different ways on DNA or on messenger RNA coding for bradykinin, in particular by blocking the binding or the progression of the ribosomes along the messenger RNA, by cleaving the messenger RNA with RNase H, or by preventing the transport of the messenger RNA from the nucleus to the cytoplasm, or alternatively by preventing maturation of the messenger RNA.

According to the invention, anti-bradykinin antibodies or soluble bradykinin receptors, anti-bradykinin-receptor antibodies or bradykinin receptor antagonists can also be used.

Preferably, according to the invention, a compound which interferes with the effects of bradykinin by binding to its receptor (B1 or B2), preferably to the B2 receptor, is used.

Even more preferably, a bradykinin antagonist chosen from:

D-Arg, [Hyp3, D-Phe7]bradykinin (NPC567),

[Thi5,8, D-Phe7]bradykinin,

D-Arg, [Hyp3, Thi5,8, D-Phe7]bradykinin,

N-α-adamantaneacetyl-D-Arg, [Hyp3, Thi5,8, D-Phe7]-bradykinin, des-Arg9, [Leu8]bradykinin, P-guanidobenzoyl, [Hyp3, Thi5, D-Tic7, Oic8]-bradykinin, (S 16118), D-Arg, [Hyp3, Thi5, D-Tic7, Oic8]bradykinin (HOE 140), D-Arg, [Hyp3, D-Hype (transpropyl)7, Oic8]bradykinin (NPC 17731)

is used according to the invention.

The modified peptide preferably used according to the invention is D-Arg, [Hyp3, Thi5, D-Tic7, Oic8]bradykinin (HOE 140).

The effective amount of bradykinin antagonists to use corresponds, needless to say, to the amount required to obtain the desired result. A person skilled in the art is thus capable of evaluating this effective amount, which depends on the nature of the antagonist used and on the person thus treated.

In order to give an order of magnitude, according to the invention, in a cosmetic composition, the antagonist can be present at a concentration of between $10^{-12}$ M and $10^{-3}$ M, and preferably between $10^{-9}$ M and $10^{-4}$ M. In the preparation of medicinal products, the inhibitor can be present at a concentration of between $10^{-12}$ M and 1 M, and preferably between $10^{-6}$ M and $10^{-1}$ M.

The medicinal product according to the invention can be administered parenterally, enterally or topically. Preferably, the medicinal product is administered topically.

The physiologically acceptable medium in which the active agent is used according to the invention can be anhydrous or aqueous. The term anhydrous medium is understood to refer to a solvent medium containing less than 1% water. This medium can consist of a solvent or a mixture of solvents chosen more particularly from $C_2$–$C_4$ lower alcohols such as ethyl alcohol, alkylene glycols such as propylene glycol, and alkyl ethers of alkylene glycols or of dialkylene glycols, in which the alkyl or alkylene radicals contain from 1 to 4 carbon atoms. The term aqueous medium is understood to refer to a medium consisting of water or of a mixture of water and another physiologically acceptable solvent chosen, in particular, from the organic solvents mentioned above. In the latter case, when they are present, these other solvents represent 5 to 95% of the weight of the composition approximately.

It is possible for the physiologically acceptable medium to contain other adjuvants commonly used in the cosmetic or pharmaceutical field, such as surfactants, thickeners or gelling agents, cosmetic agents, preserving agents, basifying or acidifying agents well known in the prior art, and in sufficient amounts to obtain the desired presentation form, in particular a relatively thickened lotion, a gel, an emulsion or a cream. The use can optionally be in a form pressurized as an aerosol or vaporized from a pump-dispenser bottle.

It is also possible to use, in combination with the active agent, compounds which further improve the activity on hair regrowth and/or on slowing down hair loss, and which have already been described for this activity.

Among the latter compounds, mention may be made more particularly, in a non-limiting manner, of:

nicotinic acid esters including, in particular, tocopheryl nicotinate, benzyl nicotinate and $C_1$–$C_6$ alkyl nicotinates such as methyl or hexyl nicotinate;

pyrimidine derivatives such as 2,4-diamino-6-piperidinopyrimidine 3-oxide or "Minoxidil" described in U.S. Pat. No. 4,596,812 or alternatively the many derivatives thereof, or such as 6-amino-1,2-dihydro-1-hydroxy-2-imino-4-piperidinopyrimidine and the derivatives thereof as described in patent U.S. Pat. No. 4,139,619;

agents which promote hair regrowth such as those described by the Applicant in the European patent application published under the number 0648488;

antibacterial agents such as macrolides, pyranosides and tetracyclines, and in particular Erythromycin;

calcium antagonists such as Cinnarizine and Diltiazem;

hormones, such as oestriol or analogues, or thyroxine and salts thereof;

steroidal anti-inflammatory agents, such as corticosteroids (for example: hydrocortisone);

antiandrogenic agents such as oxendolone, spironolactone and diethylstilbestrol;

5-α-reductase antagonists;

OH-radical scavengers such as dimethyl sulphoxide.

Other compounds can also be added to the above list, namely, for example, Diazoxide, Spiroxazone, phospholipids such as lecithin, linoleic acid, linolenic acid, salicylic acid and the derivatives thereof described in French patent FR 2,581,542, such as salicylic acid derivatives bearing an alkanoyl group having from 2 to 12 carbon atoms in position 5 of the benzene ring, hydroxycarboxylic acids or ketocarboxylic acids and the esters thereof, lactones and the corresponding salts thereof, anthralin, carotenoids, eicosatetraynoic acid and eicosatriynoic acid or the esters and amides thereof, and vitamin D and the derivatives thereof.

It may also be envisaged that the composition comprising at least one bradykinin antagonist is in liposomal form, as described in particular in patent application WO 94/22468 filed on Oct. 13, 1994 by the company Anti Cancer Inc. Thus, the antagonist encapsulated in the liposomes can be delivered selectively to the hair follicle.

The cosmetic composition according to the invention is to be applied to alopecic areas of an individual's scalp and hair, and is optionally left in contact for several hours and a rinsing operation is optionally carried out. It is possible, for example, to apply the composition containing an effective amount of at least one bradykinin antagonist in the evening, to keep it in contact throughout the night and optionally to shampoo the hair in the morning. These applications can be repeated daily for one or more months depending on the individual.

Thus, the subject of the present invention is also a process for the cosmetic treatment of the hair and/or the scalp, characterized in that it consists in applying a composition comprising an effective amount of at least one bradykinin antagonist to the hair and/or the scalp, in leaving this composition in contact with the hair and/or the scalp and optionally in carrying out a rinsing operation.

The treatment process has the characteristics of a cosmetic process insofar as it allows the aesthetic appeal of the hair to be enhanced by making it more vigorous and improving its appearance.

Examples, which should not be considered as limiting the scope of the invention in any way, will now be given by way of illustration.

EXAMPLE 1

Measurement of the Effect of Minoxidil and of Minoxidil Sulphate on the Increase in Intracellular Calcium Concentration Induced by Bradykinin a) Culturing Keratinocytes of the Outer Sheath of Human Hair Follicles:

This procedure is a variant of that described by YANG et al., J. Invest. Dermatol., 1993, 101 (5), 652–659.

After decontamination, a lifting scalp biopsy is treated with dispase in a proportion of 2.4 units/ml for 20 hours at 4° C.

The outer sheath of the hair follicles (ORS) is then isolated by dissection, followed by treatment with 0.125% trypsin for 30 minutes at 37° C.

The cells thus prepared are then cultured in conditioned Green medium for 6 days.

The cells thus prepared are then cultured in Green medium condition for 6 days.

The cells are then placed on glass slides 10 mm in diameter and cultured in KGM medium.

b) Measurement of the Intracellular Calcium Concentration:

The measurements are taken according to the procedures used conventionally by those skilled in the art and which are found, for example, in Cellular Calcium: A Practical Approach, published by J. G. McCormack and P. H. Cobbold; IRL PRESS (1991).

The cells are incubated for 1 hour at 37° C. in 10 mM HEPES buffer, 5 mM KCl, 140 mM NaCl, 10 mM glucose, 1 mM $MgCl_2$, 2 mM $CaCl_2$ with 5 μM FURA 2 acetomethyl ester and Pluronic (5 mg/10 ml).

After rinsing in the buffer, the slides are placed in an adapted support and the reading is taken using a PERKIN ELMER LS 50 B spectrofluorimeter at 37° C.

The cells are preincubated with or without Minoxidil or Minoxidil sulphate, for at least 120 seconds before the injection of 1 μM bradykinin.

c) Results:

| Product | c.c.* in μM | % Inhibition (1 μM bradykinin) |
| --- | --- | --- |
| Minoxidil | 10 | 0% |
|  | 50 | 15% |
|  | 100 | 25% |
|  | 1000 | 31% |
| Minoxidil sulphate | 10 | 0% |
|  | 50 | 31% |

-continued

| Product | c.c.* in $\mu M$ | % Inhibition (1 $\mu M$ bradykinin) |
|---|---|---|
| | 100 | 54% |
| | 1000 | 70% |

Minoxidil and Minoxidil sulphate inhibit the increase in intracellular calcium concentration induced by bradykinin, thus acting as bradykinin antagonists.

EXAMPLE 2

Examples of compositions to be applied on the hair and/or the scalp. These compositions can be prepared by simple mixing.

Composition 1: Spray:
  D-Arg, [Hyp3, Thi5, D-Tic7, Oic8]-$5 \times 10^{-6}$ g bradykinin (HOE 140)
  Minoxidil 0.5 g
  95° Ethanol 55.1 g
  Propylene glycol 22.8 g
  Fragrance qs
  Demineralized water qs 100 g Composition 2: Daily Lotion:
  D-Arg, [Hyp3, D-Phe7]bradykinin $12.5 \times 10^{-6}$ g (NPC567)
  2,4-diaminopyrimidine 3-oxide 0.75 g
  95° Ethanol 30 g
  Fragrance qs
  Dyes qs
  Demineralized water qs 100 g Composition 3: Liposomal Gel:
  Natipide II$^1$ (i.e. 2 g of 10 g phospholipides)
  D-Arg, [Hyp3, D-Phe7]bradykinin (NPC567) $3 \times 10^{-4}$ g
  Carbomer 0.25 g
  Triethanolamine qs pH=7
  Preserving agents qs
  Demineralized water qs 100 g
  $^1$Water/alcohol/lecithin mixture from the company Natterman Composition 4: Liposomal Gel:
  Natipide II$^1$ (i.e. 2 g of 10 g phospholipides)
  D-Arg, [Hyp3, Thi5, D-Tic7, Oic8]- $5 \times 10^{-5}$ g bradykinin (HOE 140)
  Carbomer 0.25 g
  Triethanolamine qs pH=7
  Preserving agents qs
  Demineralized water qs 100 g
  $^1$Water/alcohol/lecithin mixture from the company Natterman Composition 5: Niosomal Gel:
  Chimexane NS$^1$ 1.8 g
  Monosodium stearoylglutamate 0.2 g
  des-Arg9, [Leu8]bradykinin $7.5 \times 10^{-4}$ g
  Carbomer 0.2 g
  Triethanolamine qs pH=7
  Preserving agents qs
  Fragrances qs
  Demineralized water qs 100 g
  $^1$Nonionic surfactant sold by the company Chimex.

Composition 6: Nisomal Lotion:
  Chimexane NL$^1$ 0.475 g
  Cholesterol 0.475 g
  Monosodium stearoylglutamate 0.05 g
  D-Arg, [Hyp3, Thi5,8, D-Phe7]-$10^{-3}$ g bradykinin
  Preserving agents qs
  Dyes qs
  Fragrance qs
  Demineralized water qs 100 g
  $^1$Nonionic surfactant sold by the company Chimex.

Composition 7: Care Cream: O/W emulsion
  Cetylstearyl alcohol/cetylstearyl 5 g
  alcohol oxyethylenated with 33 mol of oxyethylene (80/20)
  Glyceryl monostearate 1.5 g
  Cetyl alcohol 0.75 g
  Liquid petroleum jelly 10 g
  Polydimethylsiloxane 0.75 g
  Glycerol 4 g
  Preserving agents qs
  D-Arg, [Hyp3, Thi5, D-Tic7, Oic8]-$5 \times 10^{-3}$ g bradykinin (HOE 140)
  Demineralized water qs 100 g

What is claimed is:

1. A method to promote or stimulate hair growth and/or delay hair loss, said method comprising administering an effective amount of at least one bradykinin antagonist to promote or stimulate hair growth and/or delay hair loss to an individual in need thereof, wherein said bradykinin antagonist binds to a B1 and/or B2 bradykinin receptor.

2. A method to promote or stimulate hair growth and/or delay hair loss comprising administering an effective amount of at least one bradykinin antagonist in an amount effective to promote, stimulate and/or delay hair loss wherein said bradykinin antagonist is selected from
  D-Arg (Hyp3, D-Phe7)-bradykinin (NPC567);
  (Thi5,8, D-Phe7)-bradykinin;
  D-Arg, (Hyp3, Thi5,8, D-Phe7)-bradykinin;
  N-α-adamantaneacetyl-D-Arg (Hyp3, Thi5,8, D-Phe7)-bradykinin;
  des-Arg9, (Leu8)-bradykinin;
  P-guanidobenzoyl (Hyp3, Thi5, D-Tic7, Oic8)-bradykinin (S 16118);
  D-Arg (Hyp3, Thi5, D-Tic7, Oic8)-bradykinin (HOE 140); and
  D-Arg, (Hyp3, D-Hype (transpropyl)7, Oic8)-bradykinin (NPC 17731).

3. The method of claim 2 wherein said bradykinin antagonist is D-Arg (Hyp3, Thi5, D-Tic7, Oic8)-bradykinin (HOE 140).

4. A process for the cosmetic treatment of the hair and/or scalp comprising administering an effective amount of a cosmetic composition wherein said composition comprises at least one bradykinin antagonist in a physiologically acceptable medium, in an amount effective to promote or stimulate hair growth and/or delay hair loss in said subject wherein said bradykinin antagonist binds to a B1 and/or B2 bradykinin receptor.

5. The process for cosmetic treatment of the hair and/or scalp of claim 4 wherein said bradykinin antagonist is selected from D-Arg (Hyp3, D-Phe7)-bradykinin (NPC567);
(Thi5,8, D-Phe7)-bradykinin;
D-Arg, (Hyp3, Thi5,8, D-Phe7)-bradykinin;
N-α-adamantaneacetyl-D-Arg (Hyp3, Thi5,8, D-Phe7)-bradykinin;
des-Arg9, (Leu8)-bradykinin;
P-guanidobenzoyl (Hyp3, Thi5, D-Tic7, Oic8)-bradykinin (S 16118);
D-Arg (Hyp3, Thi5, D-Tic7, Oic8)-bradykinin (HOE 140); and
D-Arg, (Hyp3, D-Hype (transpropyl)7, Oic8)-bradykinin (NPC 17731).

6. The process for cosmetic treatment of the hair and/or scalp of claim 4 wherein said antagonist is D-Arg (Hyp3, Thi5, D-Tic7, Oic8)-bradykinin (HOE 140).

7. The process of claim 4 wherein said cosmetic composition is administered to the hair and/or scalp.

8. The process of claim 6 wherein said cosmetic composition is left in contact with the hair and/or scalp.

* * * * *